US009957384B2

(12) United States Patent
Suzuki et al.

(10) Patent No.: US 9,957,384 B2
(45) Date of Patent: May 1, 2018

(54) HEAT-SHRINKABLE TUBE HAVING TEARABILITY

(71) Applicant: Junkosha Inc., Kasama (JP)

(72) Inventors: Masahiro Suzuki, Kasama (JP); Kohei Yuri, Kasama (JP); Tomoyo Okubo, Kasama (JP)

(73) Assignee: Junkosha Inc., Kasama-shi (JP)

( * ) Notice: Subject to any disclaimer, the term of this patent is extended or adjusted under 35 U.S.C. 154(b) by 0 days. days.

(21) Appl. No.: 15/228,129

(22) Filed: Aug. 4, 2016

(65) Prior Publication Data

US 2017/0058115 A1    Mar. 2, 2017

(30) Foreign Application Priority Data

Aug. 24, 2015   (JP) ................................ 2015-164679
Jun. 29, 2016   (JP) ................................ 2016-128577

(51) Int. Cl.
   *C08L 27/18*     (2006.01)
   *A61L 29/04*     (2006.01)
   *A61M 25/00*     (2006.01)

(52) U.S. Cl.
   CPC ............. *C08L 27/18* (2013.01); *A61L 29/041* (2013.01); *A61L 29/049* (2013.01); *A61M 25/00* (2013.01); *C08L 2205/025* (2013.01); *C08L 2207/02* (2013.01); *C08L 2207/04* (2013.01)

(58) Field of Classification Search
   CPC ........... A61M 25/0023; A61M 25/0009; A61L 29/041; F16L 11/04; B65D 71/08; B29C 47/0023; B29C 65/74; B29C 66/40; B29C 65/02; B29K 2023/10; Y10T 428/1328; B29L 2023/22; B29L 2023/00; B65B 53/02
   USPC ..................................... 428/35.7, 35.9, 411.1
   See application file for complete search history.

(56) References Cited

U.S. PATENT DOCUMENTS

| 4,879,362 A    * | 11/1989 | Morgan ................ C08F 214/26 428/407 |
| 2001/0031594 A1* | 10/2001 | Perez ........................ B32B 5/26 442/339 |
| 2014/0255633 A1* | 9/2014  | Suzuki .................. A61L 29/041 428/35.1 |

(Continued)

FOREIGN PATENT DOCUMENTS

| JP | 11323053  A | 11/1999 |
| JP | 5839310   B1 | 11/2015 |

(Continued)

*Primary Examiner* — James C Yager
*Assistant Examiner* — Kevin C Ortman, Jr.
(74) *Attorney, Agent, or Firm* — The Webb Law Firm

(57) ABSTRACT

Provided is a heat-shrinkable tube having tearability, which is made of a fluororesin, particularly, a tube having excellent tear straightness and high heat-shrinkability at low temperature. The tube is a heat-shrinkable tube having tearability, which includes, as a base resin, a copolymer including at least tetrafluoroethylene and hexafluoropropylene as constituent monomers, and as a resin other than the base resin, a copolymer including at least tetrafluoroethylene and hexafluoropropylene as constituent monomers, in which a thickness of an entanglement unit of a polymer observed at a cross-section in a longitudinal direction of the tube is 9 μm or less, and has excellent tear straightness and high heat-shrinkability.

6 Claims, 9 Drawing Sheets

(56) References Cited

U.S. PATENT DOCUMENTS

2015/0354732 A1* 12/2015 Roof ................. B65B 53/02
138/118

FOREIGN PATENT DOCUMENTS

| WO | 2013077452 A1 | 5/2013 | |
|----|---------------|--------|---|
| WO | WO-2013077452 A1 * | 5/2013 | ........... A61L 29/041 |

* cited by examiner

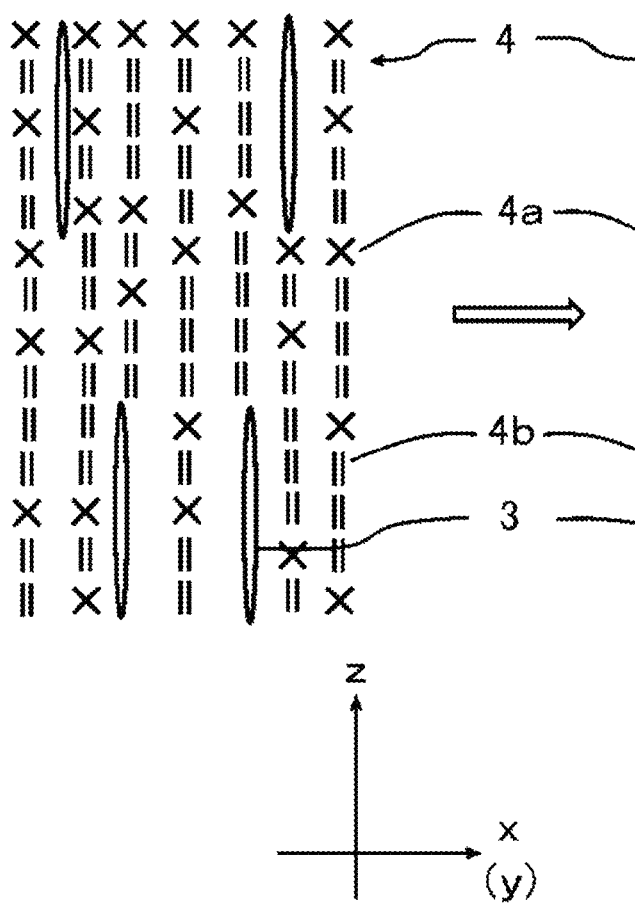

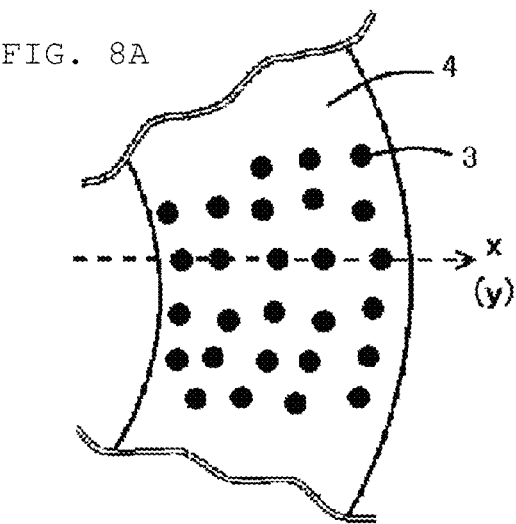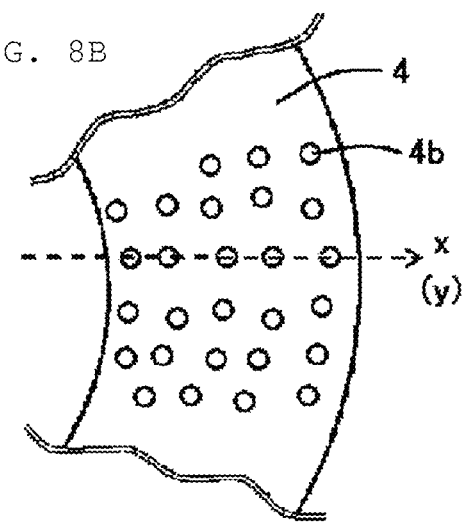

HEAT-SHRINKABLE TUBE HAVING TEARABILITY

CROSS-REFERENCE TO RELATED APPLICATIONS

This application claims priority to Japanese Patent Application Nos. 2015-164679 and 2016-128577 filed Aug. 24, 2015, and Jun. 29, 2016, respectively, the disclosures of which are hereby incorporated in their entirety by reference.

BACKGROUND OF THE INVENTION

Field of the Invention

The present disclosure relates to a heat-shrinkable tube having tearability, which is made of a fluororesin, and particularly to a tearable tube having heat-shrinkability, in which a material for the tube is composed of a thermoplastic fluororesin.

Description of Related Art

Tubes having tearability have been used as a protective member until various articles came into use. Among them, tearable tubes made of a fluororesin have characteristics of the fluororesin such as heat resistance, chemical resistance, water and oil repellency, non-adherence, and self-lubricity, which may not be obtained by using tearable tubes made of a hydrocarbon-based synthetic resin. With these characteristics, the tearable tubes are used as protective tubes for precision instrument and electronic parts, or tubes for medical device introduction for introducing a catheter, a guide wire, and the like into the body, and assembly jigs such as a catheter, and when the tubes are no longer necessary, the tubes can be torn and removed. In particular, tearable tubes having heat-shrinkability enable internal articles to be securely protected, but the heat-shrinkage rate needs to be high in order to sufficiently adhere a heat-shrinkable tube to the internal articles. Further, recently, there is a need for a heat-shrinkable tube which can be sufficiently shrunk at a lower temperature for a shorter period of time in order to minimize effects of heat applied when the heat-shrinkable tube is shrunk on internal articles. In addition, the tubes are required to be easily torn without using a special instrument. Tearable tubes in the related art are provided with a cut on the surface in a longitudinal direction throughout the full length thereof, and are not easily torn at all.

International Publication No. WO2013/077452 suggests a tube which can be torn without requiring an excessive cut and has high heat-shrinkage rate. However, when the diameter of a tube to be needed is narrowed depending on the use, there is a problem in that the tear straightness becomes insufficient. When the diameter of the tube is narrow, it is difficult to uniformly apply force which cuts open (tears) the tube in a lateral direction to the tube. Even when tear force is non-uniformly applied, excellent tear straightness is needed in order to surely tear the tube throughout the full length thereof.

In addition, when the tube is used as an assembly jig such as a catheter, high heat-shrinkability is required in addition to tear straightness, and simultaneously, since the tube affects the dimensional accuracy of a completely assembled catheter, dimensional accuracy when the tube is shrunk is required. Errors of several percentages (%) in both internal diameter and length when the tube is shrunk are significantly problematic.

PRIOR ART DOCUMENT

Patent Document

[Patent Document 1] International Publication No. WO2013/077452
[Patent Document 2] Japanese Patent Application No. 2015-52533

SUMMARY OF THE INVENTION

Technical Problem to be Solved

In consideration of the above problems, an object of the present disclosure is to enhance particularly the heat-shrinkage rate of a heat-shrinkable tube having tearability described in Patent Document 2, and to provide a tube having a heat-shrinkable rate of 48% or more when the tube is heated to 200° C., a heat-shrinkable rate of 38% or more when the tube is heated to 160° C., and excellent tear straightness when the tube is torn after the tube is shrunk.

Means to Solve the Technical Problem

As a result of extensive studies to achieve the object, the present inventors have found that excellent tear straightness was obtained when the thickness of the entanglement unit of a polymer constituting a tube reaches a specific range, and in addition, the heat-shrinkage rate thereof could be significantly enhanced by blending specific resins, thereby completing the present disclosure. That is, the present disclosure relates to a heat-shrinkable tube having tearability, which includes, as a base resin, a copolymer including at least tetrafluoroethylene and hexafluoropropylene as constituent monomers, and as a resin other than the base resin, a copolymer including at least tetrafluoroethylene and hexafluoropropylene as constituent monomers, in which the thickness of the entanglement unit of a polymer observed at the cross-section in a longitudinal direction of the tube is 9 μm or less.

Effects of the Invention

Since the tube of the present disclosure has excellent tear straightness, even a tube having a small diameter, to which it is difficult to uniformly apply tear force when the tube is removed, can be easily torn and removed. Further, since the tube of the present disclosure has high heat-shrinkage rate, even a tube having a small diameter forms a cut with an internal article (a covering material to be covered) and thus is easily inserted into the internal article.

BRIEF DESCRIPTION OF THE DRAWINGS

FIG. 5A is torn, for the tube of the present disclosure by dispersion control of THV dispersion particles.

FIG. 7A is a view schematically illustrating a molecular state in the tube, for the tube of the present disclosure by entanglement control of FEP molecules.

FIG. 7B is a view illustrating the route of propagation when FIG. 7A is torn, for the tube of the present disclosure by entanglement control of FEP molecules.

FIGS. 8A and 8B are views schematically illustrating the x-y cross-section of the tube of the present disclosure illustrated in FIG. 2. FIG. 8A is a schematic view of a portion of the tube in which the entanglement strength of the molecules by dispersion control of THV dispersion particles is controlled and FIG. 8B is a schematic view of a portion of the tube in which the entanglement strength of the molecules by entanglement control of FEP molecules is controlled.

DESCRIPTION OF THE INVENTION

The present disclosure uses, as a base resin, a copolymer (hereinafter, referred to as 'FEP(1)'.) including at least tetrafluoroethylene and hexafluoropropylene as constituent monomers. These resins have a melting point of 200° C. or more, and a tube having excellent heat resistance is obtained by the melting point. The present disclosure uses, as an additive to enhance tearability to be described below, a copolymer (hereinafter, referred to as 'FEP(2)'.) including at least tetrafluoroethylene and hexafluoropropylene as constituent monomers. In order to enhance tearability, the FEP (2) is a resin which is different from the FEP (1), but both resins have at least tetrafluoroethylene and hexafluoropropylene as constituent monomers, and thus have a similar molecular structure. Since the two resins have a similar molecular structure, and the adhesive property of the two resins is increased, a tube composed of FEP (1) and FEP (2) is hardly torn when the tube is expanded during the manufacturing process thereof and can be more significantly expanded, so that during the heat shrinkage which is a process in which the tube is returned to the original shape, the return amount is more greatly increased, and the heat-shrinkage rate is enhanced more than that of the conventional tube.

In the present disclosure, it is preferred that the base resin or the resin other than the base resin is a copolymer including perfluoroalkyl vinyl ether as a constituent monomer. The perfluoroalkyl vinyl ether as a constituent monomer causes high heat-shrinkage rate at low temperature.

A polymer material is present in a state where the molecular chains of the molecules constituting the material are entangled like a ball of thread. The entangled state of these molecules is maintained even in a molded body obtained by molding the polymer material, so that physical properties of the molded body are significantly affected by the entangled structure of the molecules. The present disclosure is an improvement of Patent Document 1, which was also filed by the Applicant of this disclosure to provide a heat-shrinkable tube having excellent tear straightness by controlling the entanglement strength of the molecules constituting the tube. The heat-shrinkable tube having excellent tear straightness of the present disclosure is characterized in that the thickness of the entanglement unit of a polymer observed at the cross-section in a longitudinal direction of the tube is 9 µm or less.

Figure 1:
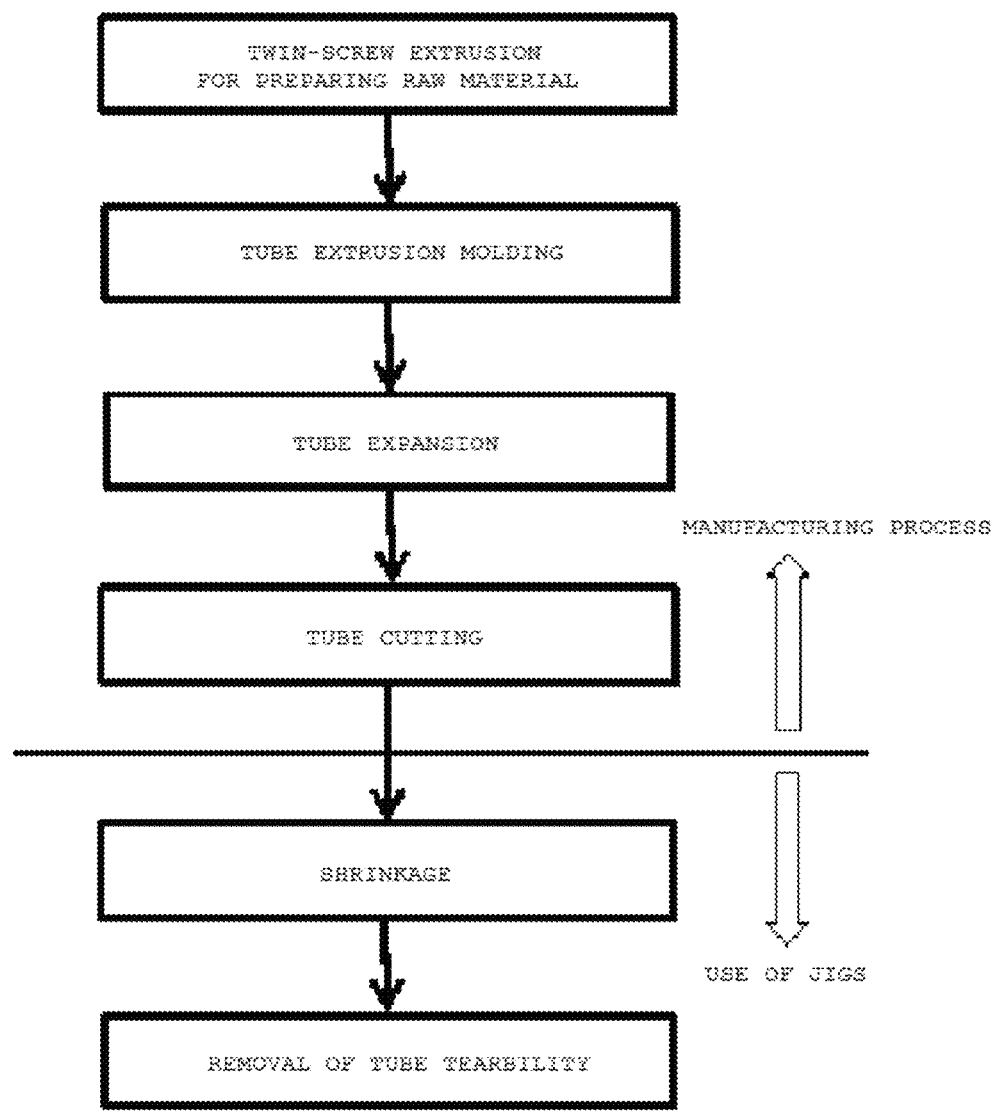
FIG. 1 is a flowchart illustrating an example of a manufacturing process of a tube of the present disclosure.

The heat-shrinkable tube having tearability of the present disclosure is prepared by the process illustrated in FIG. 1 as an example. The flowchart from the preparation of raw materials to the tube cut is a process of manufacturing a product, and the shrinkage and the removal of the tube tearability are equivalent to the user's process. When the heat-shrinkable tube having characteristics of the present disclosure is to be manufactured, it is necessary to control the entanglement strength of the molecules as described below. When the entanglement strength of the molecules is to be controlled, there are usually two methods. One is to control the entanglement strength by dispersion control of an additive for enhancing tearability, and the other is to control the entanglement strength by entanglement control of the molecules of a base resin.

Hereinafter, the effects of the entanglement structure of the molecules on the tearability of the tube will be described using the drawings.

Figure 2:
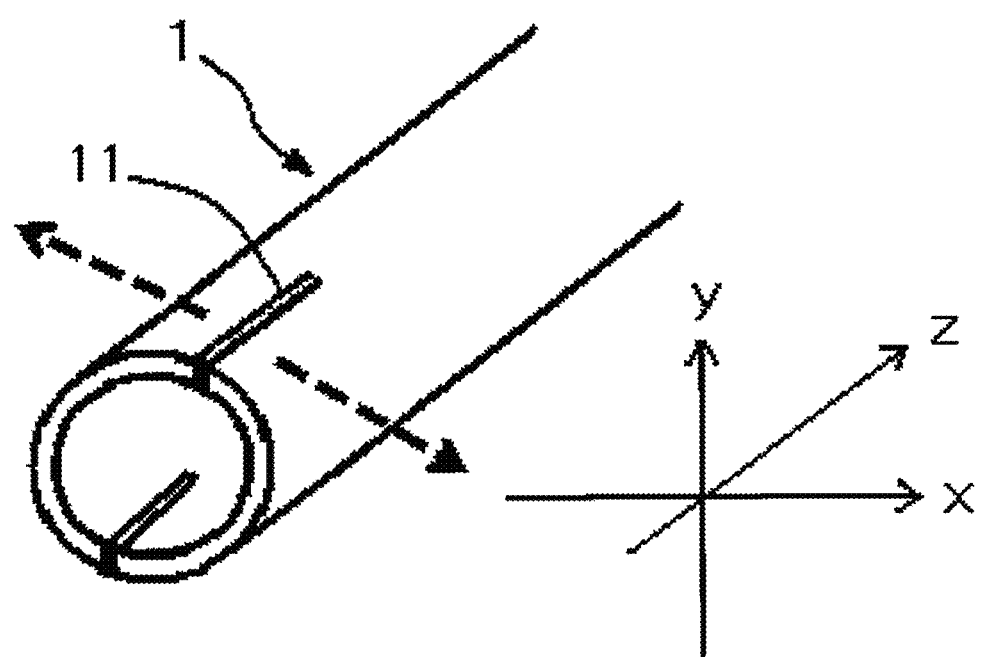
FIG. 2 is a view illustrating a method for observing the cross-section of the tube of the present disclosure.
Figure 3:
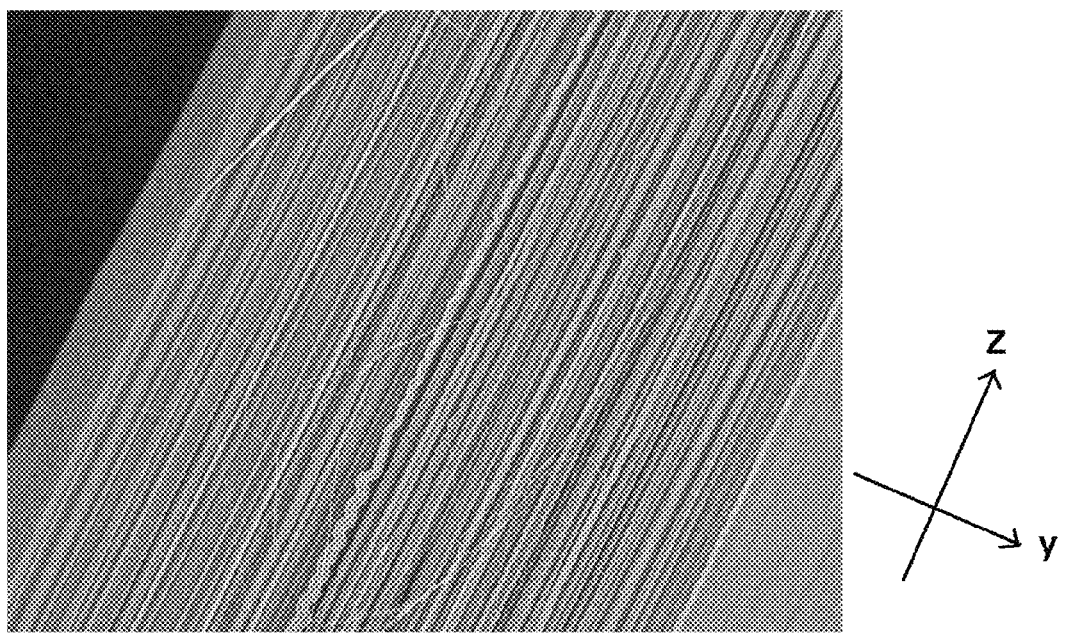
FIG. 3 is a photograph of the cross-section of the tube of the present disclosure in the longitudinal direction.

In FIG. 2, the method for observing the cross-section of the heat-shrinkable tube will be described. Here, the tube of the present disclosure is a tearable tube, so that the cross-section thereof may be observed by tearing the tube. When a tube 1 is torn, the tube 1 is torn in the z-axis direction (in FIG. 2, the longitudinal direction of the tube is defined as the z-axis direction) by applying tensile strength to a cutting line 11 placed at the center of the tube in a direction of widening the cutting line. As an example, FIG. 3 illustrates a photograph of the cross-section including the z-axis when the tube is torn in the z-axis.

A method for controlling the entanglement strength by dispersion control of the additive for enhancing tearability will be shown below.

In the heat-shrinkable tube of the present disclosure, FEP (1) is used as a base resin. As an additive to enhance tearability, FEP (2), a polymer which is incompatible with the base resin, is used.

Examples of the FEP (2) include THV, an ethylene-tetrafluoroethylene-hexafluoropropylene copolymer (hereinafter, referred to as 'EFEP'.), and the like. The addition amount of FEP (2), which is added to FEP (1) is preferably 20 wt % or less based on the total amount including FEP (1). When the addition amount is more than 20 wt %, it is difficult to increase the expansion rate of the tube, and it becomes difficult to be able to obtain a high heat-shrinkage rate such as a heat-shrinkage rate of 48% or more when the tube is heated to 200° C. and a heat-shrinkage rate of 38% or more when the tube is heated to 160° C.

As an aspect of the present disclosure, a tube using a tetrafluoroethylene-hexafluoropropylene copolymer (hereinafter, referred to as 'FEP'.) as FEP (1) and THV as FEP (2) will be exemplified and described below.

Figure 4A:
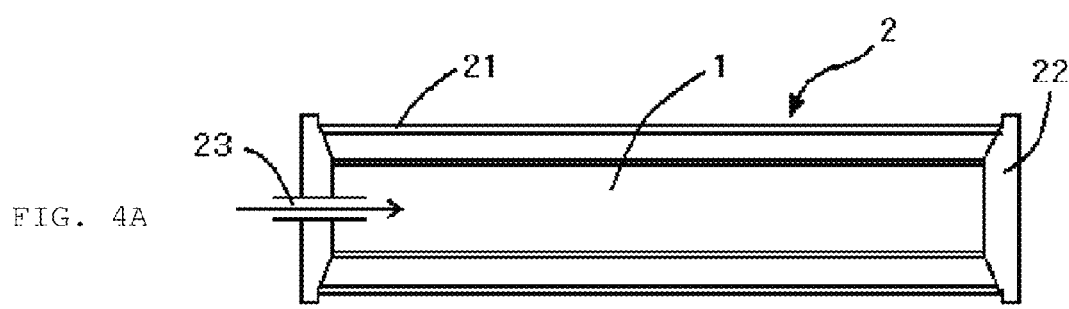
FIG. 4A is a cross-sectional schematic view of an expandable jig used in the expansion of the tube, illustrating an expandable jig with a type which fixes both ends of the tube.
Figure 9:
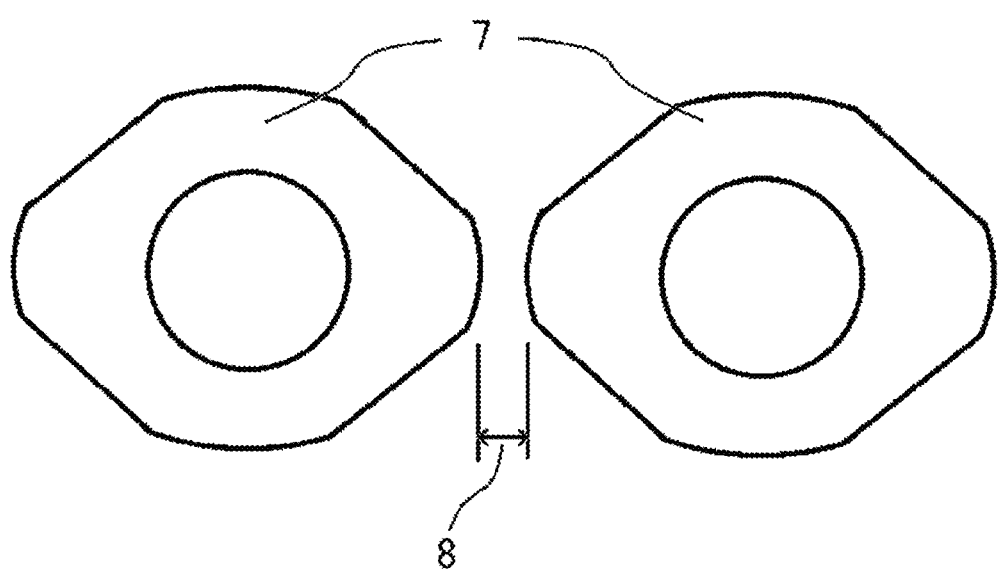
FIG. 9 is a view explaining a gap of a screw of a twin-screw extruder.

The tube is molded by a process illustrated in FIG. 1. In a twin-screw extruder used for dispersing THV in FEP, a pattern and a gap are adjusted in order to finely disperse THV (hereinafter, referred to as 'fine dispersion'). As illustrated in FIG. 9, a gap 8 refers to an interval of thread parts of a screw 7. It is preferred to provide the pattern of the screw with a staying part. This is molded into the tube by a single-screw extruder. The molded tube is expanded by using an expandable jig 2 illustrated in FIG. 4A. A tube 1 is allowed to pass through a pipe for regulating the outer diameter (hereinafter, referred to as 'outer diameter regulating pipe 21') to fix both ends of the tube 1 to sealing jigs 22 at both ends of the outer diameter regulating pipe 21 and seal the tube 1. The tube 1 is expanded in a diameter direction by injecting a compressed gas into the tube from an injection port 23 to pressurize the inside of the tube 1 while heating an expandable jig 2 which fixes the tube 1.

Figure 5A:
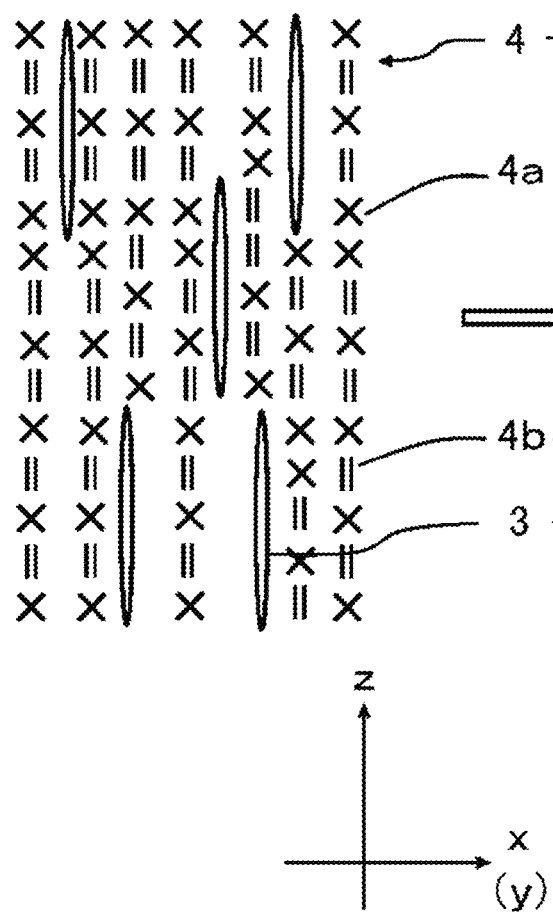
FIG. 5A is a view schematically illustrating a molecular state in the tube, for the tube of the present disclosure by dispersion control of THV dispersion particles.

FIG. 5A schematically illustrates a molecular state in the tube when the tube prepared as explained above is shrunk. The THV dispersion particle 3 is present in a state where the particle is stretched in a longitudinal direction of the tube (the longitudinal direction of the tube is defined as the z-axis direction in FIGS. 5A and 5B) after the tube is extrusion molded, and then, the void is generated at a portion of the interface between FEP 4 and the THV dispersion particle 3 by expanding the inner diameter of the tube. The void portion generated by the expansion is in a state where FEP 4 and the THV dispersion particle 3 are dissociated, and is in a state where the entanglement of molecules is cut off. A plurality of voids is present in the tube by finely dispersing THV. Further, the state where FEP molecules are entangled becomes a state where the entanglement of FEP molecules is easily disentangled by expansion because a portion 4a where FEP molecules are entangled and a portion 4b where molecules are not entangled are present after the tube is extrusion molded. Specifically, since the fluororesin FEP has low cohesive force among the molecular chains, the molecular chains are easily slipped and the molecular chains are slid by expansion in a portion where FEP molecules are slightly entangled, so that the entanglement of FEP molecules becomes easily disentangled.

Figure 5B:
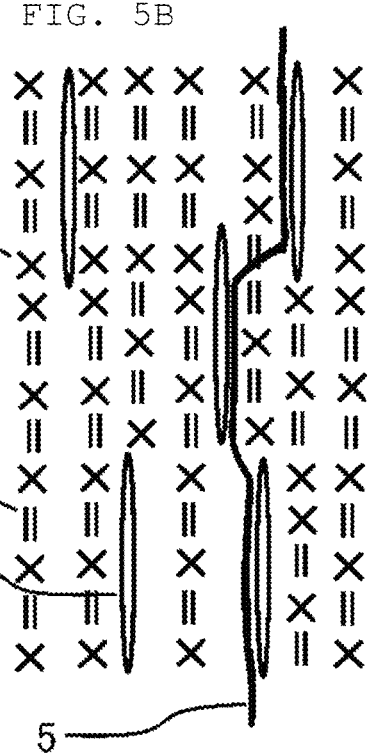
FIG. 5B is a view illustrating the route of propagation when

Since there is no entanglement of molecules in the portion of voids, the force for disentangling the entanglement of molecules (hereinafter, referred to as 'entanglement strength of molecules') is 0. Further, in a portion of the state where the entanglement of FEP molecules is easily disentangled, the entanglement strength of molecules is close to 0. A bundle of FEP molecules, which are surrounded by a portion where the entanglement strength of molecules is 0 and a portion where the entanglement strength is weak, are formed at in the tube after being expanded. When a cutting line is placed in the end portion of the tube and tear force is added to the cutting line as a starting point, the split is propagated along the bundles of FEP molecules. FIG. 5B illustrates the route 5 of propagation when FIG. 5A is torn.

In a tube in which the entanglement strength of molecules is controlled by control of dispersion of THV dispersion particles 3, bundles of molecules may be actually observed on the cross-section including the z-axis (FIG. 3 (cross-section of the tube after being expanded)).

Hereinafter, a method for controlling the entanglement strength of molecules by controlling entanglement of FEP molecules will be shown. When the entanglement of FEP molecules is to be controlled, there are usually two methods.

Figure 6:
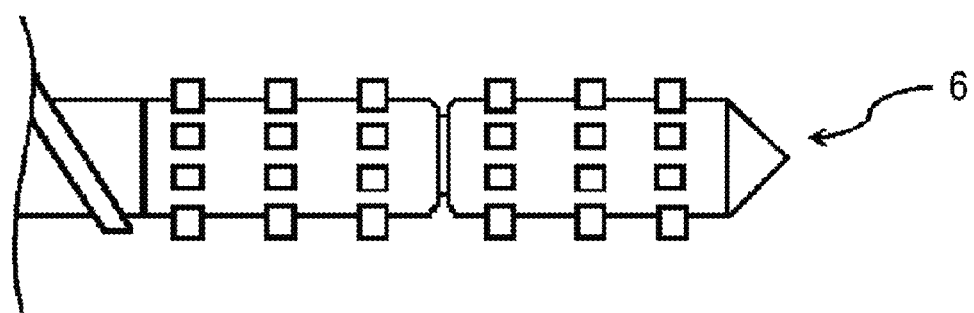
FIG. 6 is a schematic view illustrating an example of a front tip Dulmage shape of a Dulmage screw.

The first is a method of disentangling the entanglement of FEP molecules in an extrusion mold while suppressing THV from aggregating. Specifically, FEP in which THV is finely dispersed is used, and furthermore, a Dulmage screw is used as an example of the method of suppressing THV from aggregating. As a Dulmage screw, a shape is selected considering that shear force may be lowered as much as possible while suppressing the aggregation. FIG. 6 illustrates an example of the shape of the front tip of the Dulmage screw (Dulmage 6). A mold having a structure suppressing the shear rate between the dies in the screw is used. The shear force is suppressed by suppressing the shear rate, so that the entanglement of entangled molecules is disentangled in the screw part.

The second is a method of reducing the entanglement of molecules at the outlet of the extrusion mold. Specifically, molding is carried out by setting the Draw-Down-Ratio (DDR) to a large value during the extrusion molding. The DDR is obtained by the following equation.

$$DDR = \frac{((\text{Inner Diameter of Extrusion Die})^2 - (\text{Outer Diameter of Mandrel})^2)}{((\text{Outer Diameter of Tube})^2 - (\text{Inner Diameter of Tube})^2)},$$ [Equation 1]

The entanglement of molecules in the diameter direction of the tube may be decreased by increasing DDR. Herein, it is typically described that molding is achieved by setting DDR to 3 to 15 (Fluoro-resin Handbook P. 250, published by Nikkan Kogyo Shimbun, Ltd.) when a fluororesin tube is extrusion molded. However, in the heat-shrinkable tube having tearability of the present disclosure, it is preferred to set DDR to 50 or more. In the tube molded by doing so, a portion in which FEP molecules are slightly entangled in a diameter direction is present in a large amount.

However, when a tube extrusion molded by enlarging the DDR is processed with a heat-shrinkable tube, it is known that the tube is greatly shrunk in a longitudinal direction during the heat-shrinkage working of the tube. Even when the DDR is 30, it is known that shrinkage by 5% or more occurs (the official gazette of Japanese Patent Application Laid-Open No. 1999-323053), and molding in which the DDR is set to 50 or more has not been performed until now. Even in the tube of the present disclosure, when the tube is used as an assembly jig of a catheter, a large shrinkage in the longitudinal direction becomes a problem. Accordingly, it has been contrived that a heat-shrinkable tube which is not shrunk in a longitudinal direction may be obtained even in the tube extrusion molded by using the expandable jig 2 illustrated in FIG. 4B to expand the tube, and thus enlarging the DDR. The tube 1 is put into an outer diameter regulating pipe 21 by mounting a movable sealing jig 24 to one end of the tube 21. Thereafter, the inside of the tube is sealed by mounting the other end of the tube 1 to the sealing jig 22 fixed at the outer diameter regulating pipe 21. The tube 1 is expanded in a diameter direction by injecting a compressed gas into the tube from an injection port 23 to pressurize the inside of the tube 1 while heating an expandable jig 2 which fixes the tube 1. The outer diameter of the movable sealing jig 24 is smaller than the inner diameter of the outer diameter regulating pipe 21 and the tube 1 may move while sliding in the regulating pipe, so that expansion may be achieved while removing the distortion when the tube is molded in a longitudinal direction.

FIG. 7A schematically illustrates a molecular state in the tube when the tube prepared by adjusting particularly the entanglement state of molecules as explained above is expanded. When compared with FIG. 5A, the number of THV dispersion particles 3 is small and a portion 4b in which there is no entanglement of FEP molecules is present in a large amount. When compared with the case where the entanglement strength of molecules is controlled by dispersion control of THV dispersion particles 3, the portion in which the entanglement strength of molecules is 0 is present in a small amount, and the portion in which the entanglement strength of molecules is weak is present in a large amount. In the tube after being expanded, a bundle of FEP molecules surrounded by a portion in which the entanglement strength of molecules is weak and a portion in which the entanglement strength of molecules is 0 are formed. FIG. 7B illustrates the route 5 of tearing propagation when FIG. 7A is torn. The tearing of the tube is propagated along with the bundle of FEP molecules.

Even in the tube in which the entanglement strength of molecules is controlled by the entanglement control of FEP molecules, a bundle of molecules are observed on the cross-section including the z-axis in the same manner as in the tube in which the entanglement strength of molecules is controlled by dispersion control of the THV dispersion molecules.

When the addition amount of THV to be added to FEP is small, THV dispersion molecules 3 are sparsely present, and a bundle of FEP molecules are mostly formed by only the entanglement control of FEP molecules. As described above, it is possible to obtain a heat-shrinkable tube having a bundle of FEP molecules surrounded by a portion in which the entanglement strength of molecules is weak in the tube after being expanded by controlling the entanglement strength of molecules by the entanglement control of FEP molecules even when the amount of an additive is reduced or no additive is used.

FIGS. 8A and 8B schematically illustrate a portion of the x-y cross-section of the tube in FIG. 2. FIG. 8A is a schematic view of a tube in which the entanglement strength of molecules is controlled by dispersion control of THV dispersion particles 3, illustrating that THV dispersion particles 3 are scattered in FEP 4 of the base resin. FIG. 8B is a schematic view of a tube in which the entanglement strength of molecules by the entanglement control of FEP molecules is controlled, illustrating that a point 4b in which FEP molecules are not entangled is present in the base resin 4 in which FEP molecules are less entangled. The THV dispersion particle 3 of FIG. 8A and the point 4b in which FEP molecules of FIG. 8B are not entangled become a point in which the entanglement strength of molecules is 0 or close to 0, so that there is a base resin 4 having a larger entanglement strength of molecules than those of the particle 3 and the point 4 therebetween. The thickness of the bundle of FEP molecules surrounded by a portion in which the entanglement strength of molecules is weak and a portion in which the entanglement strength of molecules is 0 (hereinafter, referred to as 'thickness of the entanglement unit of a polymer') depends on the interval between the THV dispersion particle 3 or the point 4b in which FEP molecules are not entangled. The thickness of the entanglement unit of the polymer is mutually related to the tear straightness of the tube. In order to impart excellent tear straightness to the tube, the thickness of the entanglement unit of the polymer needs to be 9 μm or less. The thickness is preferably 7 μm or less, and particularly preferably 5 μm or less.

When the thickness of the entanglement unit of the polymer is too large, it means that the entanglement strength of molecules is 0 or the interval between the points close to 0 is large, and the direction of tearing propagation fluctuates, and thus, tear straightness deteriorates.

EXAMPLE (Measurement of Thickness of Entanglement Unit of Polymer)

The thickness of the entanglement unit of the polymer was calculated by measuring the shape of the cross-section of the tube in a longitudinal direction, and indicating the shape of the cross-section as a waveform. Hereinafter, the thickness will be described with reference to FIG. 3. The cross-section was measured in a vertical direction (referred to as the z-direction in the measurement of the surface shape) by using a confocal microscope (Lasertec Corporation, H1200, Objective lens 100× magnification) to scan the cross-section in the y-direction in FIG. 3. A center line was drawn by calculating a central value of the width in the z-direction of the waveform in the measurement range. The central value was calculated, except for a peak having the highest value and a peak having the smallest value of the waveform, which could be obtained in the measurement range. An interval from a point where the central line intersects with the waveform to a point where the next central line intersects with the waveform, that is, the length of the central line, which is the width of a mountain or valley, was defined as the thickness of the entanglement unit of the polymer.

(Test of Tear Straightness)

Even when a tube with a small diameter was torn, the measurement was performed by the following method in order to more clearly determine whether sufficient tear straightness could be obtained. A cutting line with a length of 40 mm was drawn at one end portion of a sample with a length of 1,000 mm. A jig was used to draw cutting line in parallel to the longitudinal direction of the tube at the center of the tube. The tube was torn at a rate of 200 mm/min from the cut portion to the other end portion of the tube. The weight of each of the two torn tubes was measured to obtain the ratio of the weights. It can be determined that tear straightness is high when the ratio is close to 50% to 50%. When the tube with a small diameter is to be torn, the ratio needs to be set within a range between 50% to 50% and 45% to 55%. Tear straightness is enhanced by setting the ratio within a range between 50% to 50% and 48% to 52%, furthermore within a range between 50% to 50% and 49% to 51%.

(Measurement of Heat-Shrinkage Rate at 200° C.)

As described below, the heat-shrinkage rate was calculated by arbitrarily taking out ten products drawn from tubes (products) having an inner diameter of 0.6 mm and a thickness of 0.24 mm, which had been expanded immediately before the tubes (tubes before expansion) were torn, measuring the inner diameter, then heating the products in a thermostat at 200° C. for 20 minutes, and measuring the inner diameter after the product was heat-shrunk.

(Heat-Shrinkage Rate,%)=((Inner Diameter Before Shrinkage)−(Inner Diameter After Shrinkage))÷(Inner Diameter Before Shrinkage)×100

(Measurement of Heat-Shrinkage Rate at 160° C.)

Samples were prepared in the same manner as in the measurement of the heat-shrinkage rate at 200° C. After the inner diameter was measured, the product was heated in a thermostat at 160° C. for 5 minutes and heat-shrunk, then the inner diameter was measured, and the heat-shrinkage rate was calculated based on the Equation.

Example 1

(Manufacture of Molding Material)

FEP (1): a tetrafluoroethylene-hexafluoropropylene-perfluoroalkyl vinyl ether copolymer (Du Pont-Mitsui Fluorochemicals Co., Ltd, FEP-130J) and FEP (2): a tetrafluoroethylene-hexafluoropropylene-vinylidene fluoride-perfluoroalkyl vinyl ether copolymer (THV: Dyneon THV815GZ) were mixed in at an FEP (1)/FEP (2) weight ratio=80/20, and the resulting mixture was sufficiently stirred by a tumbler. The mixture was introduced into a twin-screw extruder having a cylinder diameter of 20 mm, and was extruded at a screw rotation number of 45 rpm and a die temperature of 320° C. to obtain a molded pellet. For the screw, a pattern with four staying parts partially provided was used, and a combination of a gap of 0.5 mm was obtained.

(Molding of Sample Tube)

The prepared pellet was used to mold the tube by using the twin-screw extruder having a cylinder diameter of 20 mm. As the screw, a Dulmage screw was used, and the tube was molded at a screw rotation number of 10 rpm, a die temperature of 390° C., and a draw down ratio (DDR) of 50 according to the sizing plate method. A tube with an inner diameter of 0.6 mm and a thickness of 0.24 mm was obtained.

(Expansion of Sample Tube)

Figure 4B:
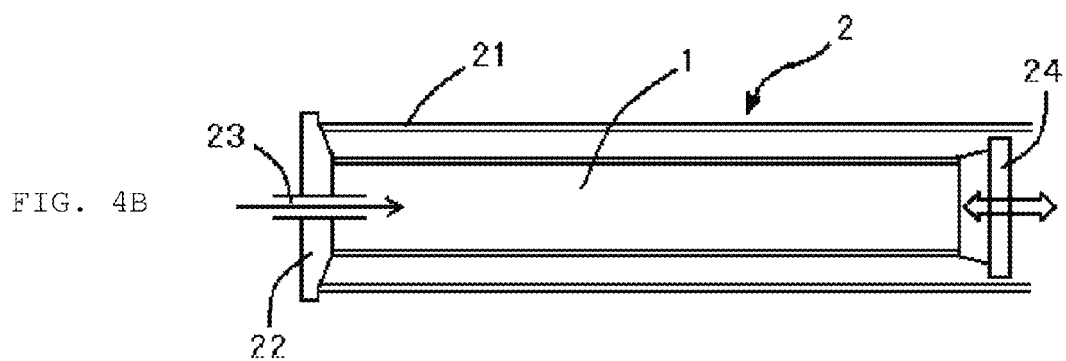
FIG. 4B is a cross-sectional schematic view of an expandable jig used in the expansion of the tube, illustrating an expandable jig with a type which fixes only one end of the tube.

The molded tube was cut into a length of 1,000 mm by mounting the tube onto an expandable jig which is the same type as in FIG. 4B, and injecting pressurized nitrogen into the internal part of the jig while heating the jig from the external part of the jig to expand the inner diameter of the tube.

(Shrinkage of Sample Tube)

Ten tubes were arbitrarily taken out from the expanded sample tubes, the inner diameters were measured, and then the tubes were heated for 20 minutes and heat-shrunk in a thermostat at 200° C., thereby producing sample tubes. The shrinkage rate was calculated by measuring the inner diameter after the shrinkage.

Further, the shrinkage rate was calculated by arbitrarily taking out ten tubes from the expanded sample tubes, measuring the inner diameter, then heating the tube in a thermostat at 160° C. for 5 minutes to heat-shrink the tubes and use the tubes as sample tubes, and measuring the inner diameter after the shrinkage.

Example 2

(Manufacture of Molding Material)

The tube was manufactured in the same manner as in Example 1, except that THV815GZ of FEP (2) was changed into an ethylene-tetrafluoroethylene-hexafluoropropylene copolymer (EFEP: dakin RP-5000).

(Molding of Sample Tube)

The experiment was carried out under the same conditions as in Example 1.

(Expansion•Shrinkage of Sample Tube)

The experiment was carried out under the same conditions as in Example 1.

Example 3

(Manufacture of Molding Material)

The tube was manufactured in the same manner as in Example 1, except that FEP (1) and FEP (2) were mixed at a FEP (1)/FEP (2) weight ratio=85/15.

(Molding of Sample Tube)

The experiment was carried out under the same conditions as in Example 1.

(Expansion•Shrinkage of Sample Tube)

The experiment was carried out under the same conditions as in Example 1.

Example 4

(Manufacture of Molding Material)

The tube was manufactured in the same manner as in Example 1, except that FEP (1) and FEP (2) were mixed at a FEP (1)/FEP (2) weight ratio=90/10.

(Molding of Sample Tube)

The tube was molded in the same manner as in Example 1, except that the draw down ratio (DDR) was set to 10.

(Expansion of Sample Tube)

The molded tube was cut into a length of 1,000 mm by mounting the tube onto an expandable jig which is the same type as in FIG. 4B, and injecting pressurized nitrogen into the internal part of the jig while heating the jig from the external part of the jig to expand the inner diameter of the tube.

(Shrinkage of Sample Tube)

The experiment was carried out under the same conditions as in Example 1.

Comparative Example 1

(Manufacture of Molding Material)

The tube was manufactured in the same manner as in Example 4, except that THV815GZ of FEP (2) was changed into a tetrafluoroethylene-ethylene copolymer (ETFE: Asahi Glass Co., Ltd, C-55 AP).

(Molding of Sample Tube)

The experiment was carried out under the same conditions as in Example 4.

(Expansion of Sample Tube)

The experiment was carried out under the same conditions as in Example 4.

(Shrinkage of Sample Tube)

The experiment was carried out under the same conditions as in Example 1.

Example 5

(Manufacture of Molding Material)

The tube was manufactured in the same manner as in Example 4, except that FEP-130J of FEP (1) was changed into a tetrafluoroethylene-hexafluoropropylene copolymer (FEP: Du Pont-Mitsui Fluorochemicals Co., Ltd FEP-100).

(Molding of Sample Tube)

The experiment was carried out under the same conditions as in Example 4.

(Expansion of Sample Tube)

The experiment was carried out under the same conditions as in Example 4.

(Shrinkage of Sample Tube)

The experiment was carried out under the same conditions as in Example 1.

For each sample tube manufactured, the thickness of the entanglement unit of the molecule was obtained based on the above-described method of measuring the thickness of the entanglement unit of the molecule. Further, tear straightness was measured based on the above-described method of testing tear straightness. The result is shown in Table 1.

TABLE 1

|  | Example 1 | Example 2 | Example 3 | Example 4 | Comparative Example 1 | Example 5 |
|---|---|---|---|---|---|---|
| FEP (1) | FEP 130J | FEP 130J | FEP 130J | FEP 130J | FEP 130J | FEP 100 |
| FEP (1) blending ratio | 80 | 80 | 85 | 90 | 90 | 90 |
| FEP (2) | THV815GZ | RP-5000 | THV815GZ | THV815GZ | C-55AP | THV815GZ |
| FEP (2) blending ratio | 20 | 20 | 15 | 10 | 10 | 10 |
| Thickness of Entanglement Unit of Molecule (μm) | 0.8 | 0.6 | 2 | 5 | 6 | 9 |
| Tear straightness (wt %) | 50:50 ○ | 50:50 ○ | 50:50 ○ | 49:51 ○ | 49:51 ○ | 52:48 ○ |
| Shrinkage rate (%) at 200° C. | 52 | 48 | 55 | 57 | 46 | 48 |

For the tubes in Examples 1 to 5 of the present disclosure, a heat-shrinkage rate of 48% or more was obtained at 200° C., and the thickness of the entanglement unit of the polymer was 9 μm or less. The ratio of the weights of the torn tubes, which exhibits tear straightness of the tube, was between 50% to 50% and 52% to 48%, and excellent tear straightness could be obtained. In this regard, Comparative Example 1 of the heat-shrinkable tube having tearability in the related art is only to obtain a heat-shrinkable tube having a heat-shrinkage of 46% at 200° C.

Next, the heat-shrinkage rate when the tube was heated to 160° C. is shown in Table 2.

TABLE 2

|  | Example 1 | Example 2 | Example 3 | Example 4 | Example 5 | Comparative Example 1 |
|---|---|---|---|---|---|---|
| Shrinkage rate (%) at 160° C. | 43 | 38 | 45 | 48 | 39 | 36 |

For the tubes in Examples 1 to 5 of the present disclosure, a heat-shrinkage of 38% or more at 160° C. was obtained. In this regard, Comparative Example 1 of the heat-shrinkable tube having tearability in the related art is only to obtain a heat-shrinkable tube having a heat-shrinkage of 36% at 160° C.

INDUSTRIAL APPLICABILITY

A tearable tube made of the fluororesin of the present disclosure has high heat-shrinkability and good tear straightness, and thus, is easily mounted during the processing and removed after the use, and is suitable as an assembly jig such as a catheter.

DESCRIPTION OF REFERENCE NUMBERS

1: Tube, 2: Expandable jig, 21: Outer diameter regulating pipe, 22: Sealing jig, 23: Injection port, 24: Movable sealing jig, 3: THV dispersion particle, 4: FEP, 5: Route of tearing propagation, 6: Dulmage, 7: Screw, 8: Gap

The invention claimed is:

1. A heat-shrinkable tube having tearability, comprising: (a) a base resin, comprising a copolymer comprising at least tetrafluoroethylene and hexafluoropropylene as constituent monomers, and (b) a resin other than the base resin, comprising a copolymer comprising at least tetrafluoroethylene and hexafluoropropylene as constituent monomers, wherein a thickness of an entanglement unit of a polymer observed at a cross-section in a longitudinal direction of the tube is from above 0 μm to 9 μm, and wherein the tube has a heat-shrinkage rate of 48% or more when being heated to 200° C. for 20 minutes.

2. The tube of claim 1, wherein the base resin is a copolymer further comprising perfluoroalkyl vinyl ether as a constituent monomer.

3. The tube of claim 1, wherein the resin other than the base resin is a copolymer further comprising perfluoroalkyl vinyl ether as a constituent monomer.

4. A heat-shrinkable tube having tearability, comprising: (a) a base resin, comprising a copolymer comprising at least tetrafluoroethylene and hexafluoropropylene as constituent monomers, and (b) a resin other than the base resin, comprising a copolymer comprising at least tetrafluoroethylene and hexafluoropropylene as constituent monomers, wherein a thickness of an entanglement unit of a polymer observed at a cross-section in a longitudinal direction of the tube is from above 0 μm to 9 μm, and wherein the tube has a heat-shrinkage rate of 38% or more when being heated to 160° C. for 5 minutes.

5. The tube of claim 4, wherein the base resin is a copolymer further comprising perfluoroalkyl vinyl ether as a constituent monomer.

6. The tube of claim 4, wherein the resin other than the base resin is a copolymer further comprising perfluoroalkyl vinyl ether as a constituent monomer.

* * * * *